(12) United States Patent
Hartman et al.

(10) Patent No.: US 8,219,191 B1
(45) Date of Patent: Jul. 10, 2012

(54) RECUMBENT STEPPING EXERCISE DEVICE WITH STIMULATION AND RELATED METHODS

(75) Inventors: Eric C. Hartman, Versailles, KY (US);
John D. Alton, Lexington, KY (US);
Tarik S. Aweimrin, Lexington, KY (US)

(73) Assignee: Customkynetics, Inc., Versailles, KY (US)

( * ) Notice: Subject to any disclaimer, the term of this patent is extended or adjusted under 35 U.S.C. 154(b) by 0 days.

(21) Appl. No.: 13/204,996

(22) Filed: Aug. 8, 2011

Related U.S. Application Data

(63) Continuation of application No. 12/250,018, filed on Oct. 13, 2008, now Pat. No. 7,996,080.

(60) Provisional application No. 60/980,199, filed on Oct. 16, 2007.

(51) Int. Cl.
*A61N 1/00* (2006.01)

(52) U.S. Cl. ............................................. 607/2

(58) Field of Classification Search ................... 607/2
See application file for complete search history.

(56) References Cited

U.S. PATENT DOCUMENTS

2007/0208392 A1* 9/2007 Kuschner et al. ............... 607/48
* cited by examiner

*Primary Examiner* — George Manuel
(74) *Attorney, Agent, or Firm* — King & Schickli, PLLC

(57) ABSTRACT

In one aspect, a device facilitates performance of a recumbent stepping exercise using stimulation. The device may include a seat for receiving a human exercise subject and foot receivers for alternately translating to and fro relative to a stationary base along a path of travel between a first position in which the legs are at least partially bent and a second position in which the legs are less bent than in the first position. An electrical stimulator is provided for facilitating the performance of the exercise by the subject moving the foot receivers alternately along the path of travel. In another aspect, adaptive feed-forward control may also be used to enhance the stepping exercise performed using the device. Related methods of performing stepping exercises are also provided.

18 Claims, 12 Drawing Sheets

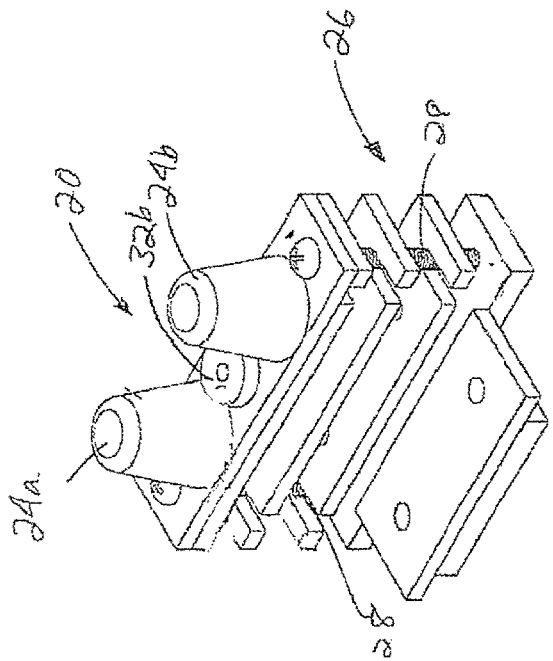
Fig. 2a
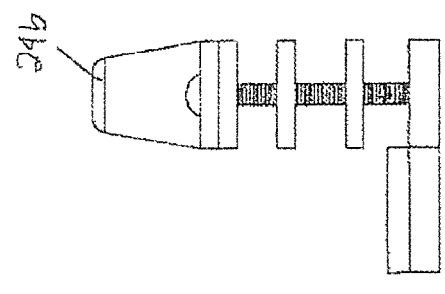
Fig. 2d
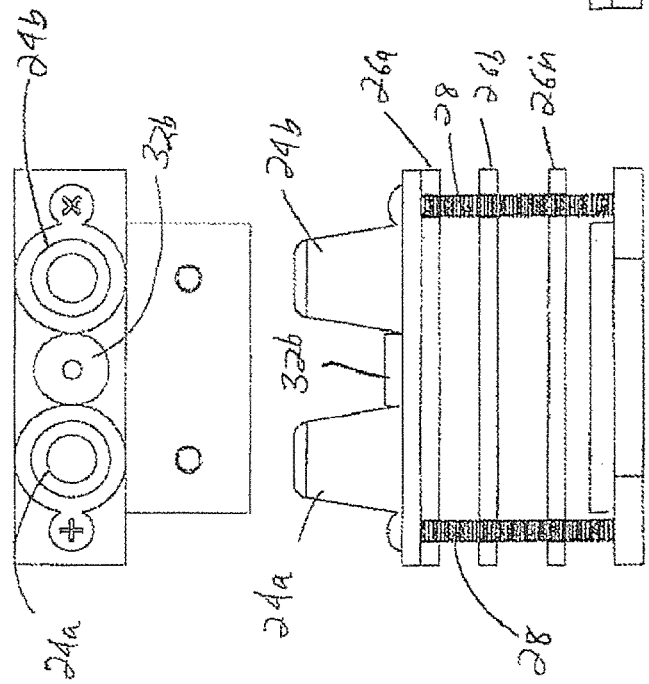
Fig. 2b
Fig. 2c

| Parameters ||
|---|---|
| Parameter | Value |
| RedZone Threshold | 204 out of 255 (80%) |
| Initial PGPS Learning Rate | 5 |
| Default Slow PGPS Learning Rate | 100 |
| Default Stimulation Frequency | 50Hz |
| Default K Coefficient | 0.5 |
| Default PGPS Filter Order | 5 |
| PGPS Number Active | 5 |
| PGPS Offset | 1 (50ms) |
| PGPS Neuron Shape | Raised Cosine |
| Sampling/Training Frequency | 20Hz (50ms) |
| Movement Definition | Ipsilateral Leg Starts Above RedZone Threshold and Contralateral Leg Ends in the RedZone in the Previous Half Cycle |
| Stimulation Ramp Hold Threshold | Leg moves 10% from starting position of the Half Cycle |

(Fixed Point)

*Fig. 12*

RECUMBENT STEPPING EXERCISE DEVICE WITH STIMULATION AND RELATED METHODS

This application claims the benefit as a Continuation of U.S. patent application Ser. No. 12/250,018, filed Oct. 13, 2008 now U.S. Pat. No. 7,996,080, titled "Recumbent Stepping Exercise Device with Stimulation and Related Methods," which claims the benefit of U.S. Provisional Patent Application Ser. No. 60/980,199, filed Oct. 16, 2007, the disclosures of which are incorporated herein by reference.

STATEMENT OF GOVERNMENT SUPPORT

This invention was supported by a grant from the National Institute of Health under contract number R43NS057890. The government may have certain rights in this invention.

COPYRIGHT STATEMENT

A portion of the disclosure of this document contains material subject to copyright protection. No objection is made to the facsimile reproduction of the patent document or this disclosure as it appears in the Patent and Trademark Office files or records, but any and all rights in the copyright(s) are otherwise reserved.

TECHNICAL FIELD

The present disclosure relates to the human exercise and rehabilitation arts and, more particularly, to devices for facilitating the performance of a seated stepping exercise with stimulation and related methods.

BACKGROUND OF THE INVENTION

Facilitating exercise using externally applied, transcutaneous stimulation, including by sending electrical pulses to contract or otherwise activate the targeted or involved muscles, is known in the art. Typically, the electrical pulses applied are generated by an external stimulator, and travel through associated wires to one or more electrode pairs placed on the skin adjacent the muscle(s) to be contracted. The electricity passing through the skin causes the targeted muscle fibers to activate or contract, even without voluntary control by the subject. Accordingly, such stimulation is frequently used in situations where the subject is incapacitated or otherwise unable to control function of the muscles, such as in the event of an injury to the brain or associated portion of the nervous system.

Despite the past use of electrical stimulation for exercising muscles, certain limitations in the application of this technology and the results produced remain. For one, no known device at present allows an exercise subject in need of rehabilitation to perform a seated (or "recumbent") alternating leg extension (or "stepping") exercise with the application of electrical stimulation. Such a regimen is considered especially beneficial for those in need of exercise for purposes of strengthening, retraining, or overall well being, but unable to walk or even stand for the time necessary to meet this need. A seated stepping exercise also better simulates the exercise movements needed to walk than, for example, a pedaling exercise using a stationary bicycle. Furthermore, completing such an exercise provides a sense of accomplishment in terms of simulating the ability to walk without the concomitant problems and sense of failure felt by those who cannot walk but might attempt to do so with the application of stimulation.

However, applying stimulation to the legs to create an alternating, or bi-lateral stepping pattern, is not a straightforward task. With a stationary bicycle, in which momentum drives the exercise, stimulation bursts may be applied to one leg simply to provide sufficient momentum to cause the other leg to also move as the result of the interconnected pedals. However, repeated stepping cannot be accomplished solely by applying such stimulation bursts to the individual legs. Also, stimulation generally cannot be used to retract the legs from an extended position. Hence, the mere application of a burst of stimulation alternately to a sitting subject's legs would simply lead to nothing productive in terms of providing the benefits of the stepping exercise and the concomitant sense of accomplishment.

Accordingly, a need is identified for a manner in which to combine the benefits achieved through electrical muscle stimulation with those of a stepping exercise, including for subjects with a full or partial inability to use the muscles of their lower extremities (and, in particular, one or both of their legs).

SUMMARY OF THE INVENTION

In one aspect, a device for use by a human subject in performing a recumbent stepping exercise using their legs, hips, knees and feet with the assistance of stimulation is disclosed. The device comprises a base and a seat supported by the base for receiving the subject. A pair of receivers are adapted for engaging the feet, and constrained for moving alternately and relative to the base along a path of travel in a stepping pattern between a first, extended position with the corresponding leg at least partially bent and the corresponding knee positioned distally from the subject's upper torso and a second, retracted position with the corresponding leg more bent than in the first position and positioned proximal the subject's upper torso. Consequently, during the exercise movement, the hip joint corresponding to each leg is being exercised.

The device further includes at least one stop located at the distal end of the path of travel for retarding the movement of at least one of the receivers. This stop thus helps to create the simulated feel of the heel of the corresponding foot making contact with the ground. The resulting movement and feeling is thus more akin to walking than pedaling a bicycle or similar types of exercises where the movement of the heel contacting the ground is not simulated or otherwise achieved.

Another part of the device is a stimulator adapted for electrically stimulating at least one muscle of at least one of the subject's legs as the receivers move along the path of travel in an alternating pattern. Preferably, the stimulator is adapted to supply electrical pulses to adjacent the targeted muscle(s). Most preferably, this is achieved using electrodes applied to a skin surface adjacent the targeted muscle(s).

Preferably, each receiver is pivotally mounted to the base by a support, and wherein the stop engages the support to halt further movement of the receiver at the first position. Most preferably, the stop comprises a height-adjustable assembly supported by the base. This height-adjustability allows for the relative movement of the receiver at the end of the forward range of movement to be adjusted as desired for a particular exercise subject.

The device may further include a controller for controlling the stimulator. Preferably, the controller controls the stimulator to apply an adaptive or fixed pattern of stimulation depending on the position of the corresponding leg within an available range of motion. Most preferably, the controller is adapted to: (a) control the stimulator during an initial phase of the stepping exercise in accordance with an initial mode; and (b) determine whether the stimulation during the initial phase results in the alternating extension of both legs for at least two cycles during this initial phase of the exercise, and then cause the stimulator to apply stimulation controlled in accordance with a maintenance mode for continuing the exercise.

Another aspect of the device is a motion sensor for sensing movement of at least one of the legs along the path of travel. A corresponding output signal is provided to the controller in controlling the stimulator to apply the adaptive or fixed pattern of stimulation. Preferably, the controller causes the stimulator to at least reduce the applied stimulation to the targeted muscle of the leg before the corresponding receiver reaches the first extended position, which may be determined using the output of the motion sensor.

In accordance with another aspect, a method for assisting a human subject in performing a recumbent stepping exercise using their legs, hips, knees and feet with the assistance of stimulation is provided. The method comprises positioning the subject on a seat with their feet on corresponding receivers. These receivers are constrained to move reciprocally along a path of travel in a stepping pattern between a first, extended position with the corresponding leg at least partially bent and the corresponding knee positioned farther away from the subject's upper torso and a second, retracted position with the corresponding leg more bent than in the first position and positioned proximate the subject's upper torso. As a result, the hip joint corresponding to each leg is being exercised during the stepping pattern.

The method further includes electrically stimulating the subject while the receivers move alternately along the path of travel. At least one stop is provided at the forward end of the path of travel for retarding the movement of at least one of the receivers. Advantageously, this simulates the feeling of the heel of the corresponding foot making contact with the ground, as would occur during walking.

Preferably, the method further includes the step of applying an adaptive or fixed pattern of stimulation depending on the position of the corresponding leg within an available range of motion. Furthermore, the method may include the step of reducing the stimulation from a previously applied level if the leg is within a predetermined portion of an available range of motion (which may involve de-activating the stimulation). Most preferably, the stimulating step is initially controlled in accordance with an initial mode, and the method further includes the step of determining whether the stimulation results in the extension of both legs for at least two cycles, and then applying stimulation controlled in accordance with a maintenance mode.

Yet another aspect is a method of performing a stepping exercise on a human subject with full or partial loss of leg muscle control. The method comprises electrically stimulating at least one muscle at a predetermined level as the legs move alternately along a path of travel between a first position and a second, extended position during the stepping exercise, sensing a parameter of the exercise, adjusting the predetermined level of electrical stimulation to a revised level based on the sensed parameter, and electrically stimulating at least a portion of the leg muscles at the revised level. Furthermore, the method may include stimulating both legs simultaneously, which can help to smooth the exercise by making the movements more natural and comfortable.

Preferably, the subject's feet each associate with movable receivers constrained to move in a reciprocating fashion, and the sensing step comprises measuring a position of the leg (which corresponds generally to the position of the receivers) as the sensed parameter. The method may further include the step of comparing the measured position with a predetermined position to determine a variation, and the adjusting step comprises determining the revised level based on the variation.

The method may further include the step of positioning the subject on a seat, and then applying an adaptive or fixed pattern of stimulation depending on the position of the corresponding leg within an available range of motion. Preferably, the method further includes the step of reducing the stimulation if the corresponding leg is within a predetermined portion of the available range of motion. Most preferably, the step of reducing the stimulation comprises stopping the stimulating step.

BRIEF DESCRIPTION OF THE DRAWING FIGURES

FIG. 1b is a side elevational view of the device of FIG. 1a;

FIGS. 2a-2d are perspective, top, and side views of a stop for use in connection with a stepping exercise device;

Figure 1A:
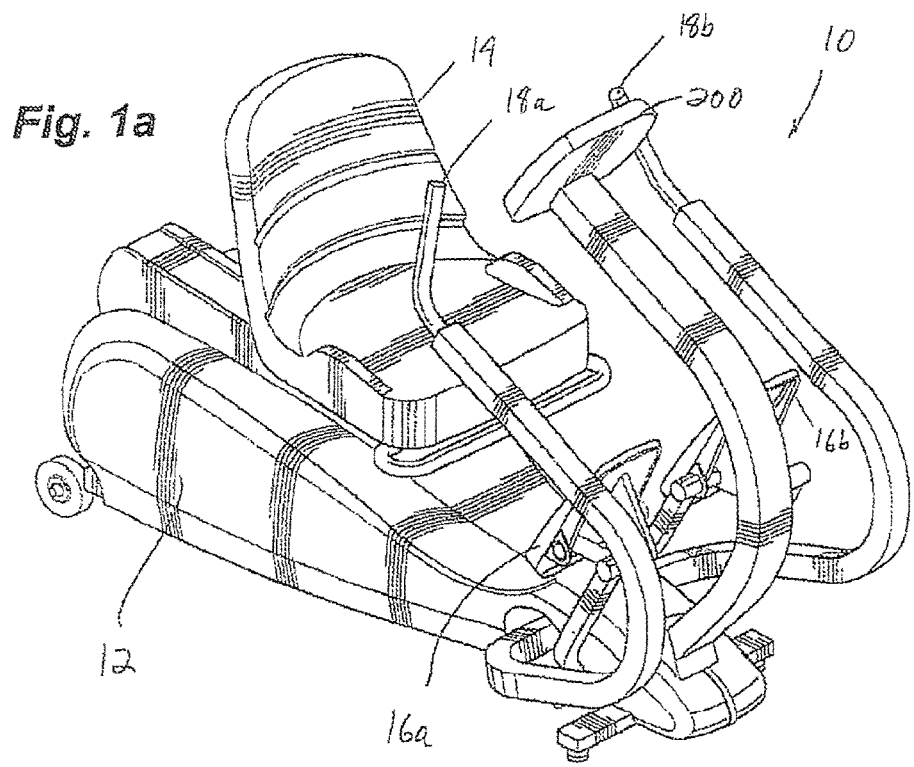
FIG. 1a is a front perspective view of an exemplary exercise device for use in performing a stepping exercise.
Figure 1B:
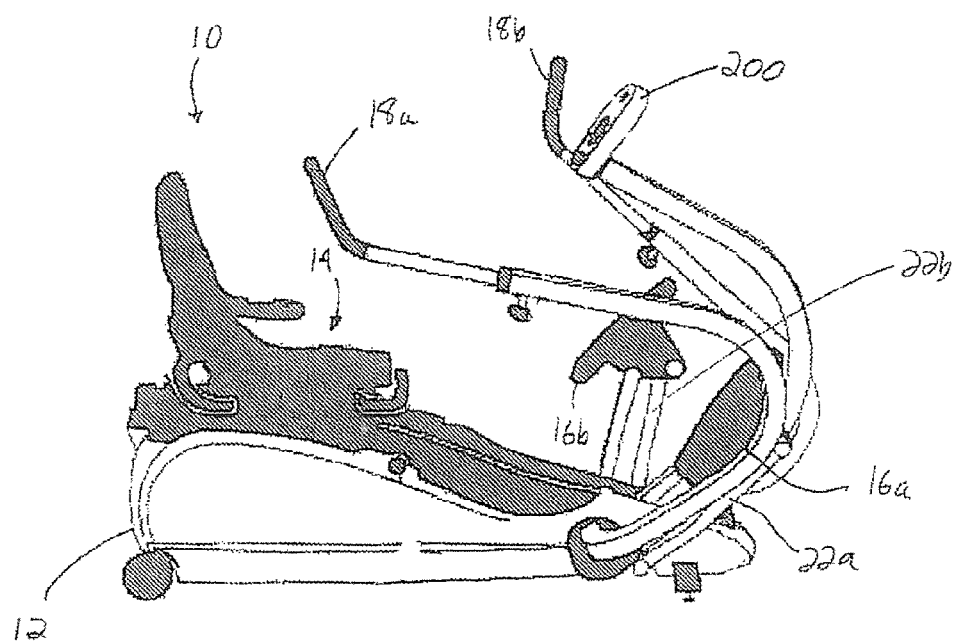
Figure 3:
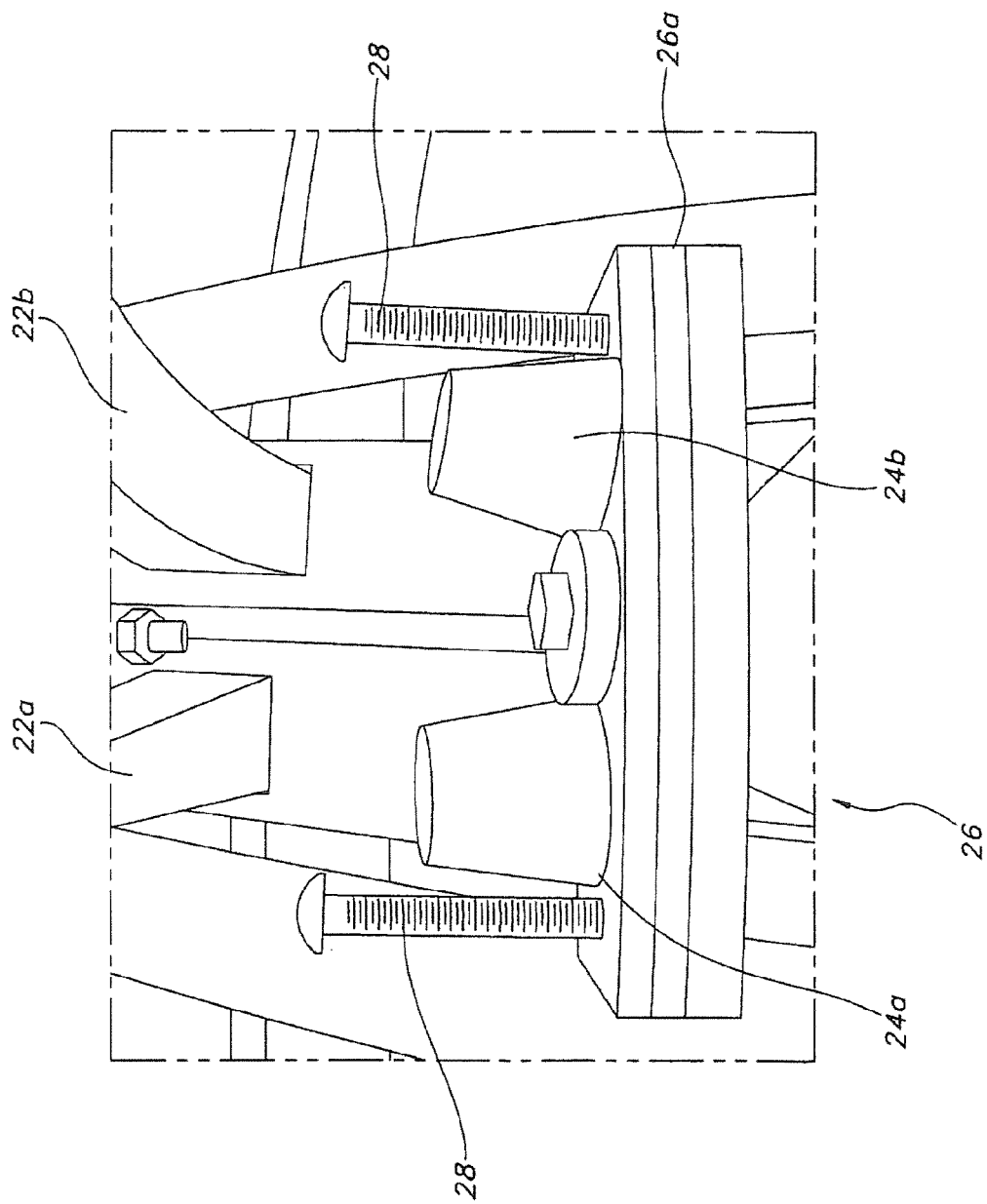
FIG. 3 illustrates the preferred mounting of the stop on the exercise device of FIGS. 1a and 1b.
Figure 6:
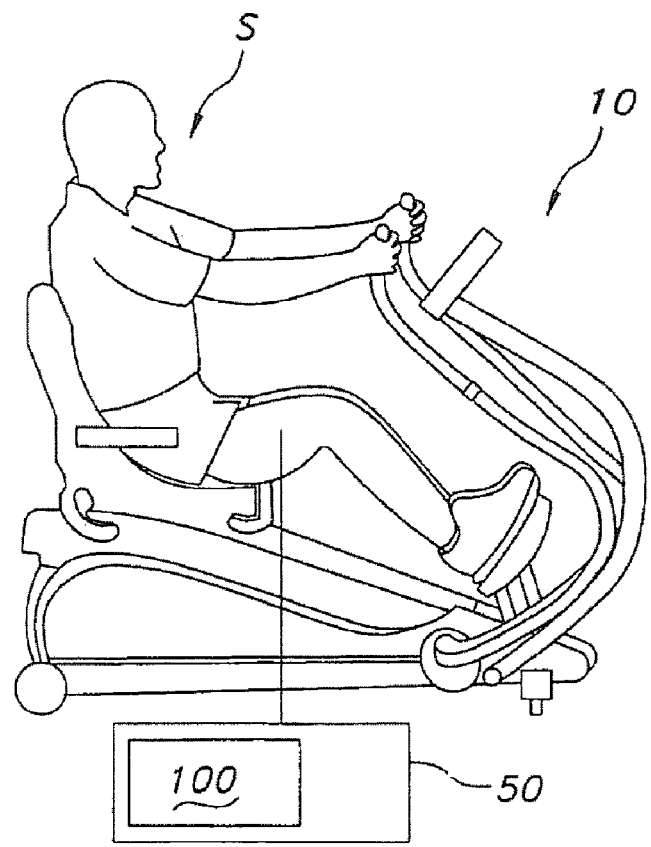
Figure 7:
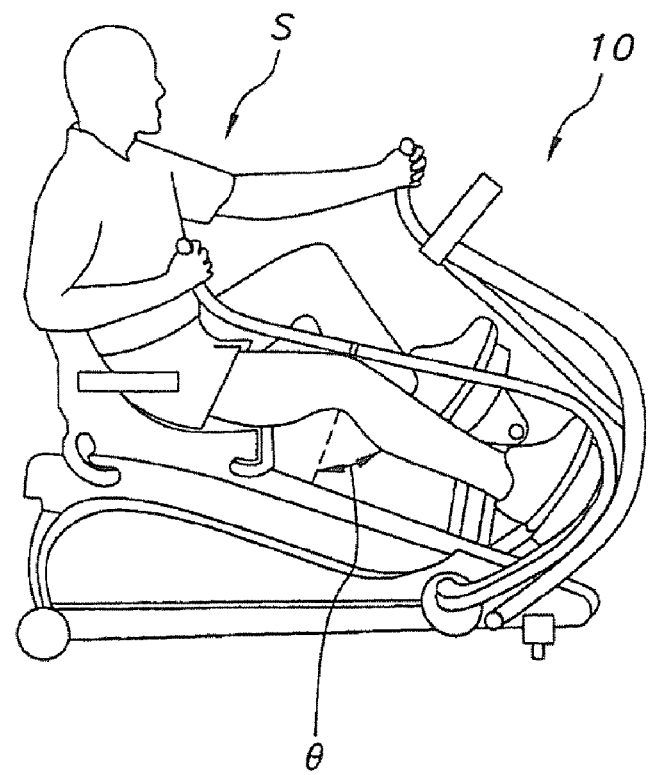
Figure 8:
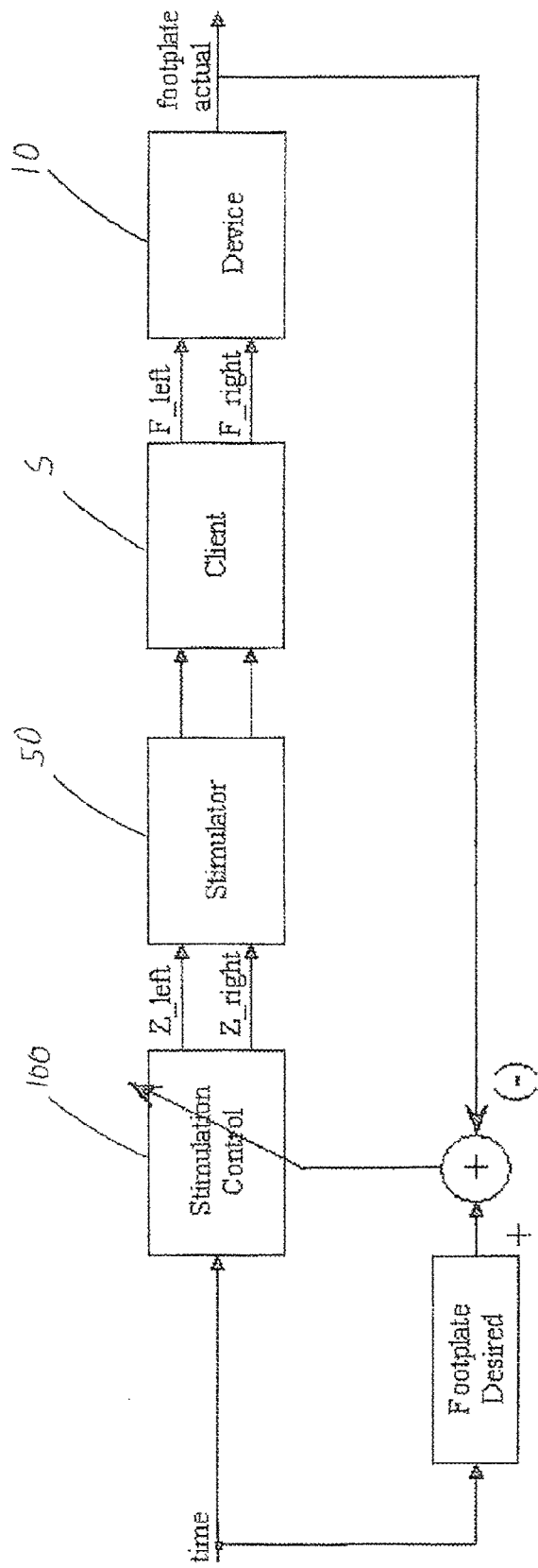
Figure 9:
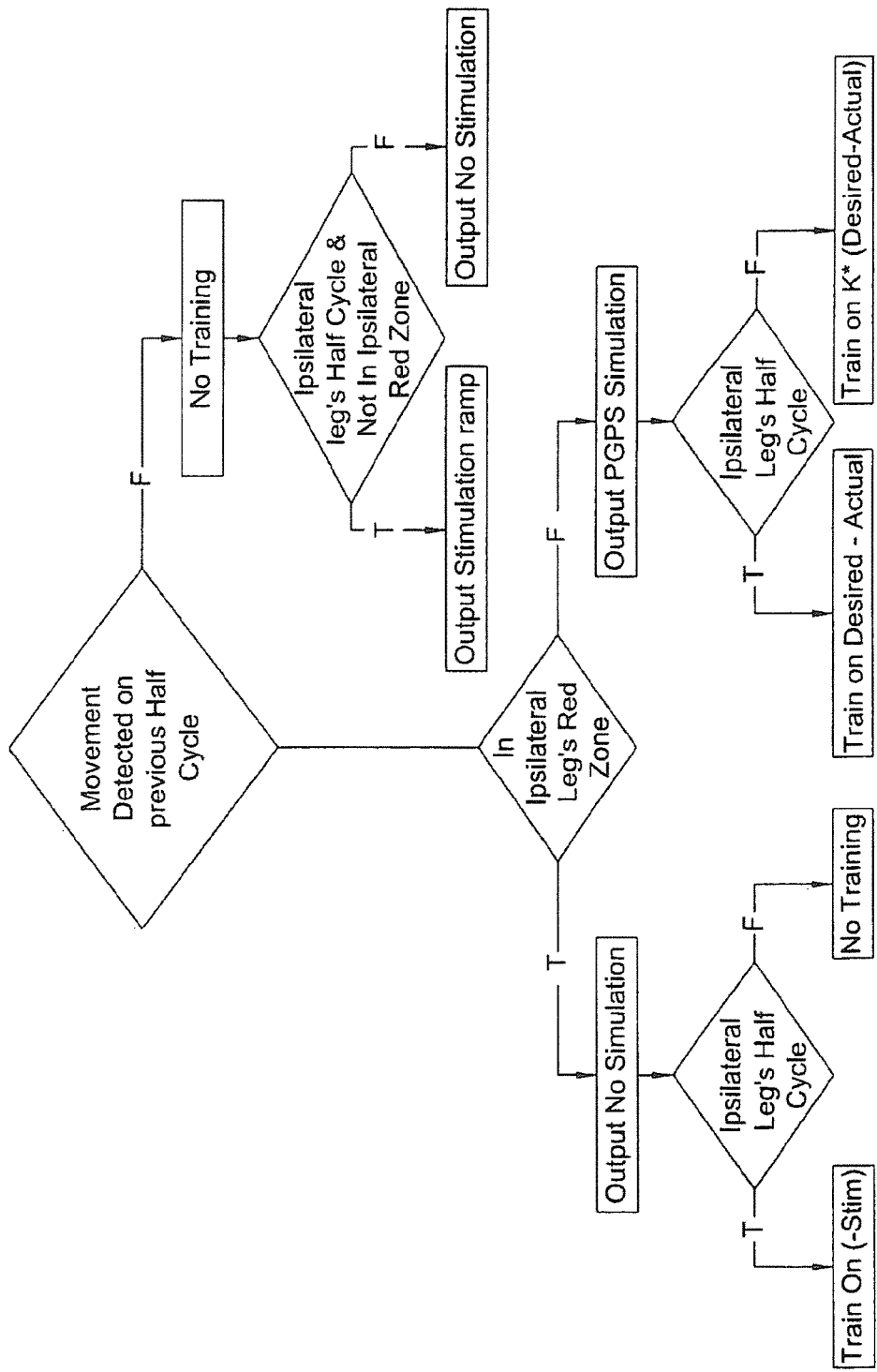
Figure 10:
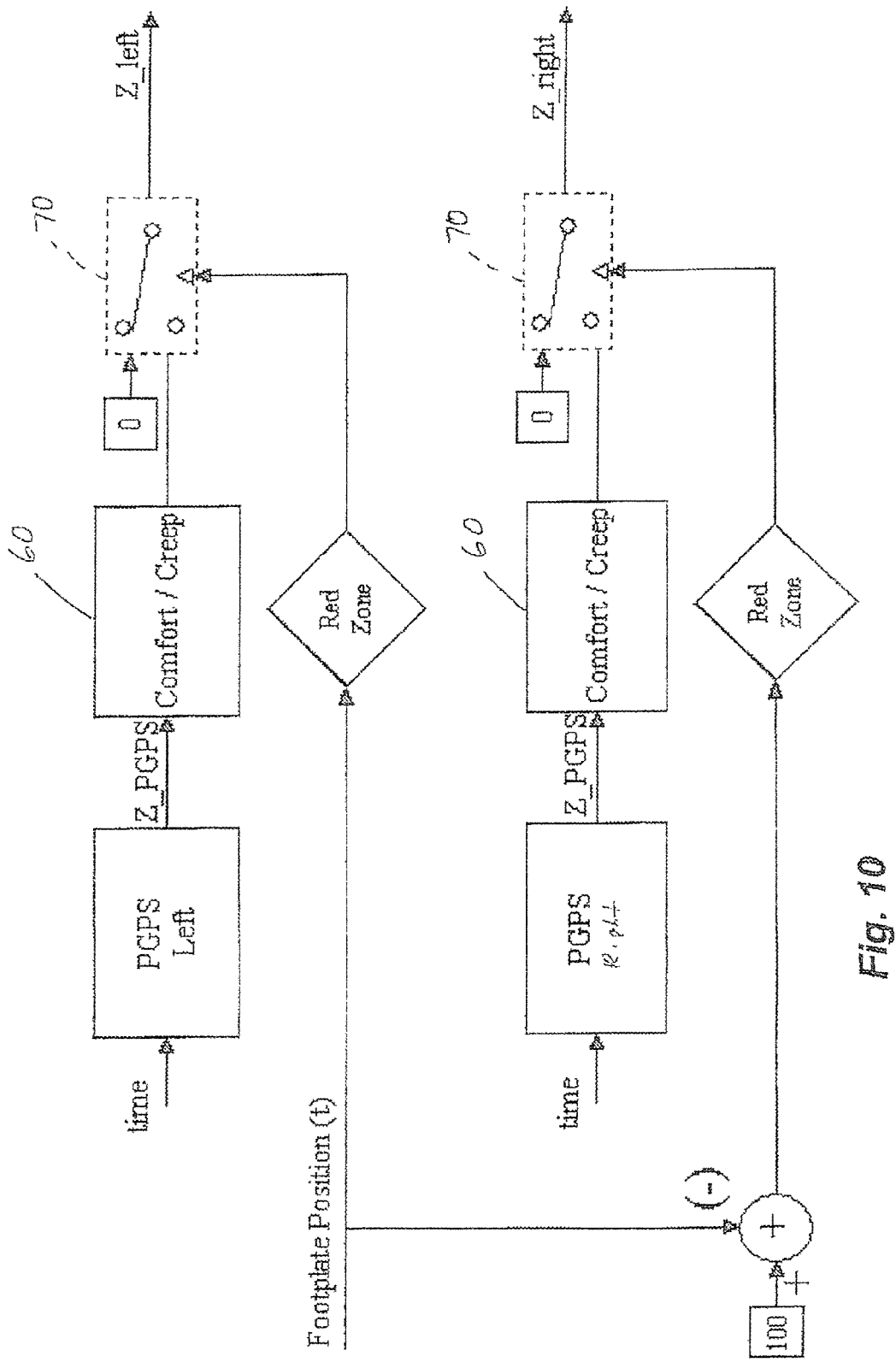
Figure 11:
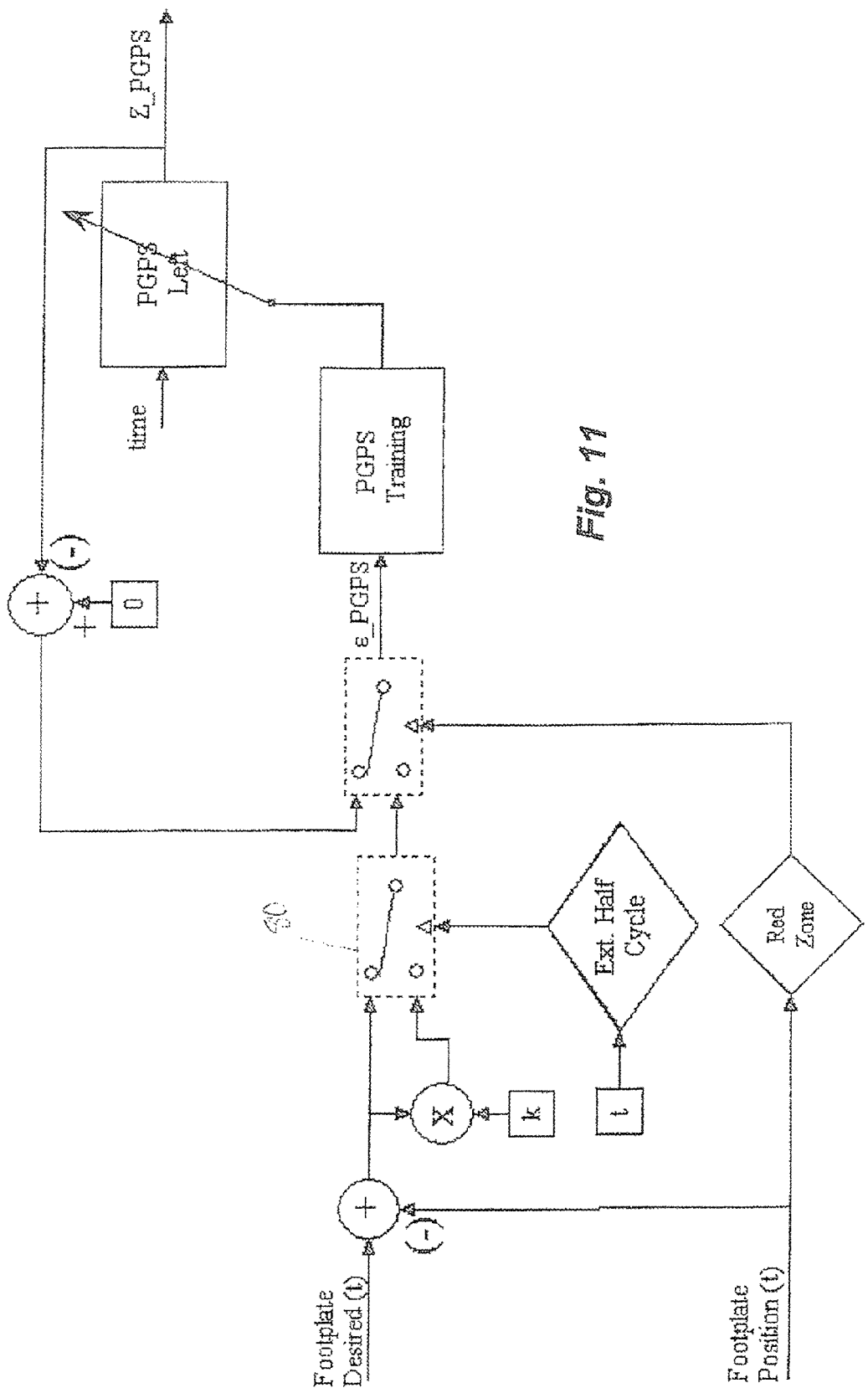
Figure 13:
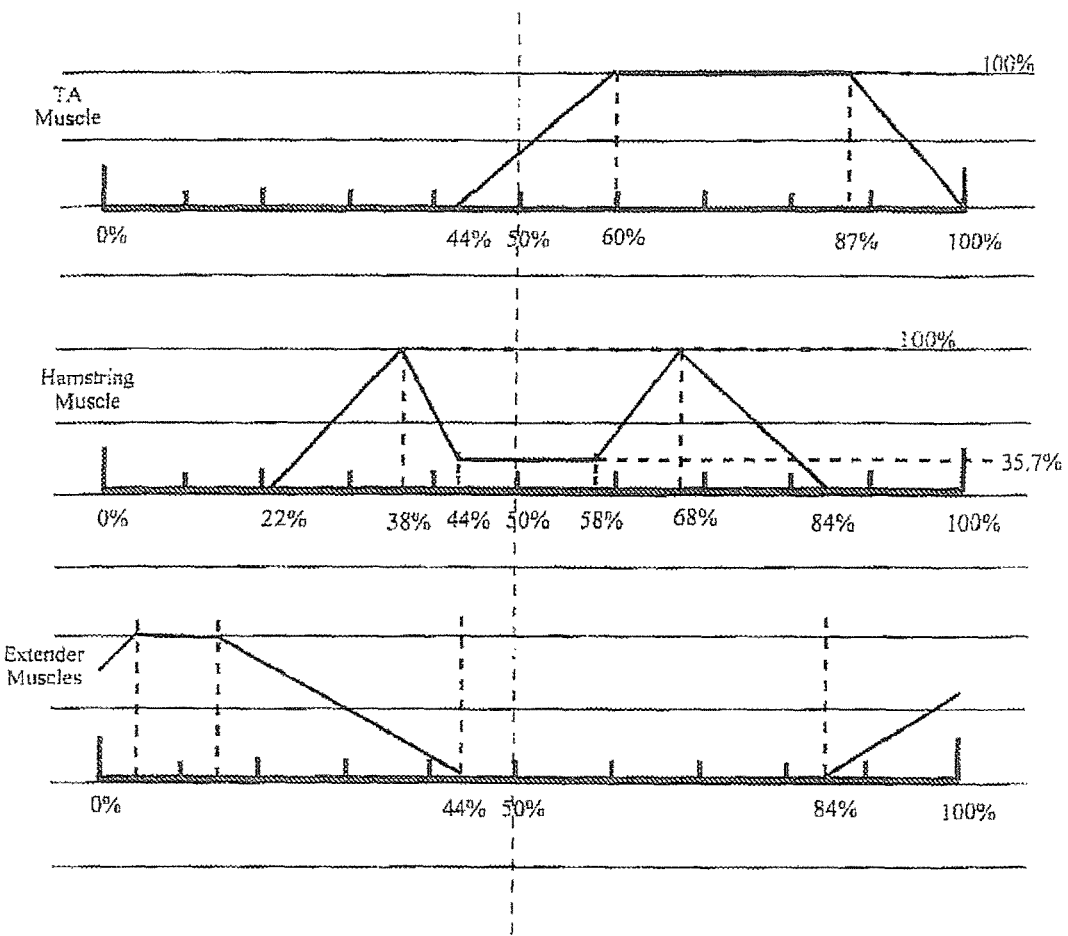

FIGS. 6 and 7 schematically illustrated a subject performing a stepping exercise using the exercise device of FIG. 1b;

FIG. 8 is a flow diagram showing one aspect of the control used to apply adaptive stimulation in the course of performing a stepping exercise;

FIG. 9 is a flow chart illustrating a preferred approach to controlling the applied stimulation based on certain parameters of the exercise;

FIGS. 10 and 11 schematically illustrate further aspects of the control;

FIG. 12 is a table listing preferred parameters associated with the control of the stimulation-based stepping exercise; and FIG. 13 graphically illustrates an exemplary preferred fixed stimulation pattern applied to various leg muscles, such as for use in accordance with a motor reeducation mode of using the proposed exercise device.

DETAILED DESCRIPTION OF THE INVENTION

Referring to FIGS. 1a and 1b, an exercise device 10 is shown for facilitating the performance of an alternating leg extension, or "stepping," exercise while the subject is seated (sometimes referred to in the vernacular as "recumbent stepping"). More specifically, the illustrated device comprises a base 12 supporting an associated seat 14 in an elevated fashion. Together, these components of the device 10 support the body weight of an exercise subject (not shown) above the ground sitting upright in a stable, secure fashion.

The base 12 may also provide support for mounted, bi-lateral foot receivers, such as plates 16a, 16b, for receiving the left and right feet of the exercise subject when seated in seat 14. The receivers or plates 16a, 16b are mounted for pivoting movement to and fro relative to the base 12 along a path of travel. The plates 16a, 16b are constrained to move reciprocally with the legs approximately 180° out of phase (that is, the movement of one plate by one leg toward the extended position moves the other plate, and hence the corresponding leg, toward the retracted position). This may be accomplished by using a linkage, belt, or like structure to connect the foot plates 16a, 16b to a rotary part (which may be associated with an inertial element and a clutch), such that the rotation in alternating directions alternates the linear movement of these plates along the path of travel between a first, extended position in which the legs are at least partially bent and a second, retracted position in which the legs are more bent that in the first position.

Preferably, the seat 14 is mounted to the base 12 in a manner that permits it to be adjusted to and fro with respect to a horizontal plane, or generally parallel to level ground. This allows for the necessary adjustments to be made to ensure that the desired range of motion can be achieved with comfort for a particular subject. The seat 14 may also be adapted to swivel in order to make it easier for the subject to assume the seated position (which can be important in situations where the subject has considerable or full loss of muscle control in their limbs).

Also supported by the base 12 are handlebars 18a, 18b. Preferably, these handlebars 18a, 18b are mounted to also allow for reciprocal movement of the arms during the stepping exercise. Although such may be desirable for enhancing the exercise provided, such handlebars 18a, 18b are considered entirely optional, and are not necessary to perform the stepping exercise in accordance with the broadest aspects of the invention.

The device 10 shown in FIGS. 1a and 1b and described above is distributed by NuStep, Inc. of Ann Arbor, Mich. under the model number TRS 4000. Such a device 10 is also generally described and shown in U.S. Pat. Nos. 6,042,518; 6,361,479; 6,666,799; and D421,075, the disclosures of which are incorporated herein by reference. However, it will be appreciated that other devices that allow for the performance of a seated or recumbent stepping exercise with the alternating extension of the legs may benefit from the various aspects of the invention disclosed.

The device 10 also includes a stop 20 providing an engagement surface for at least retarding, and preferably stopping movement of the plates 16a, 16b for receiving the subject's feet. In the illustrated embodiment, and with reference to FIGS. 2a, 2b, 2c, 2d, and 3, this stop 20 forms part of the base 12 adjacent to pivotally mounted plate supports 22a, 22b (which may comprise a linkage formed of one or more bars; compare FIGS. 1a, 1b and 2) supporting the plates 16a, 16b. The stop 20 includes at least one, and preferably a pair of spaced bumpers 24a, 24b for engaging the respective support 22a, 22b at the end, or "bottom" of the range of motion.

In many cases, it is desirable to limit the movement such that the knee joint does not lock during the stepping exercise, since it is generally not possible to unlock this joint through the use of stimulation per se. To ensure the knees do not lock in one possible embodiment, the stop 20 may be associated with a spacer assembly 26 including a plurality of spacers, such as plates 26a . . . 26n, removably associated with the assembly, such as by using fasteners 28. As should be appreciated, adding or removing the spacer plates 26a allows for adjustments to be made to the maximum movement of the supports 22a, 22b at the end of the range of motion, as desired for a particular subject pedal wing the stepping exercise with or without stimulation.

In one mode of operation, and with reference now to FIGS. 6 and 7, a subject S desiring to perform the exercise is positioned on the seat 14 with their feet engaging the corresponding plates 16a, 16b in the manner shown in FIG. 6. The stop 20 may be adjusted if necessary to ensure that at the maximum range of motion of each leg, such as the extended leg in FIG. 7, the flexion angle θ of the bent knee in the extended position is such that the leg is not fully extended (and the opposite leg is less bent). Although variance among subjects is of course possible, a typical value of the flexion angle θ to ensure a repeatable exercise with stimulation but without significantly compromising the quality of the exercise is greater than or equal to about 20° in the extended position, up to a maximum of about 60° in the fully retracted position.

Once the subject Six properly positioned, one or more of the extensor muscles of the legs are alternately electrically stimulated through one or more pairs of strategically placed electrodes using an external stimulator 50 of a type generally known in the art (such as, for example, the CK200 device available from customKYnetics, Inc. of Versailles, Ky., and described in U.S. patent application Ser. Nos. 12/164,554 and 60/937,633, the disclosures of which are incorporated herein by reference). This stimulation contracts the necessary muscles as required to cause or otherwise forcibly assist the stimulated leg in extending through a range of motion from the bent to an extended condition. Specifically, the leg to which stimulation is applied if initially in a generally relaxed or passive, bent resting position moves toward an active position in which the leg is less bent, such that the knee joint moves from proximal or closer to the upper torso to a position distal or farther away from the upper torso (and, as a result of this movement, the corresponding hip joint is advantageously being exercised). During this time, the corresponding receiver 16a, 16b moves along a generally linear path of travel between a first, retracted position corresponding to the bent leg to a second, extended position corresponding to the extended leg. The procedure is then repeated for the second, opposite leg, which as a result of the reciprocal nature of the device 10 would initially be in the generally relaxed or passive, bent resting position, and move to the extended position (with the receiver 16a, 16b following the corresponding path of travel accordingly) while the first leg returns to the bent position, closer to the torso of the subject S.

As noted above, the exemplary approach for purposes of illustrating one preferred embodiment of the invention generally involves placement of electrodes as necessary to stimulate the left and right quadriceps. As should be appreciated, the particular muscles stimulated, the location of the electrodes, the level of stimulation (that is, the amount of energy supplied per pulse), and the pulse parameters (that is, the frequency and amplitude) necessary to cause the subject to involuntarily extend their legs in such a manner may vary depending on the particular application or situation. The adjustment and application of such parameters is believed to be fully within the purview of one of ordinary skill in the electrically stimulated exercise arts.

During this dynamic loading cycle, the plates 16a, 16b of course translate longitudinally in an alternating fashion along the corresponding portion of the base 12 and the respective paths of travel while the subject S remains comfortably seated in a stable fashion. As a result, a full range of motion of the legs and associated muscles may be automatically achieved, including with the possible assistance of a subject able to perform the exercise voluntarily (in which case the stimulation may be lower or decreased, or not increased from an existing level, as a result of the voluntary contribution), and most preferably without the direct application of external force by a motive device (such as a linear cylinder). A better degree of exercise is thus afforded than would otherwise be achieved using electrical stimulation alone, and in a safe, reliable, and highly regular/repeatable fashion.

Moreover, the ability of the subject to remain comfortably seated (including with a view of the legs performing the exercise as a result of the inclined nature of the seat 14), as well as the sense of accomplishment from reciprocally moving the foot plates 16a, 16b, provides an overall better sensory experience as compared to applied stimulation while the legs remain stationary. This creates a concomitant desire to repeat the exercise successfully. Successful completion of the exercise also facilitates motor retraining due to tactile and somatosensory feedback to the spinal cord or brain.

Despite the viability of this basic technique for effecting exercise of the lower extremities with electrical stimulation of the associated muscles being advantageously afforded, it also may be desirable to combine it with a measure of automatic and adaptive feed-forward control to still further improve the quality of the resulting exercise (and without the need for active manual control provided by an assistant). To facilitate this result, and with reference now to FIG. 8, a programmable stimulation controller 100 is also disclosed. This controller 100 preferably uses known pattern generating and pattern shaping/shaper (PGPS) algorithms to output the stimulation to the corresponding legs in a selective fashion to facilitate performance of the exercise (as described in detail in the following articles, Reiss J, Abbas J J, *Adaptive Control of Cyclic Movements as Muscles Fatigue Using Functional Neuromuscular Stimulation*, IEEE Trans Neural Syst Rehabil Eng. 2001 September; 9(3): 326-30; Stites E C, Abbas J J, *Sensitivity and Versatility of an Adaptive System for Controlling Cyclic Movements Using Functional Neuromuscular Stimulation*, IEEE Trans Biomed Eng. 2000 September; 47(9): 1287-92; Reiss J, Abbas J J, *Adaptive Neural Network Control of Cyclic Movements Using Functional Neuromuscular Stimulation*, IEEE Trans Rehabil Eng. 2001 March; 8(1): 42-52; Abbas J J, Triolo R J, *Experimental Evaluation of an Adaptive Feedforward Controller for Use in Functional Neuromuscular Stimulation Systems*, IEEE Trans Rehabil Eng. 1997 March; 5(1): 12-22; and Abbas J J, Chizeck H J, *Neural Network Control of Functional Neuromuscular Stimulation Systems Computer Simulation Studies*, IEEE Trans Biomed Eng. 1995 November; 42(11): 1117-27). Using PGPS algorithms to adjust or revise the applied simulation levels, a real-time adaptive stepping exercise can thus be achieved using the disclosed techniques, which although optional may greatly improve the quality of the exercise and concomitant benefits achieved.

Figure 4:
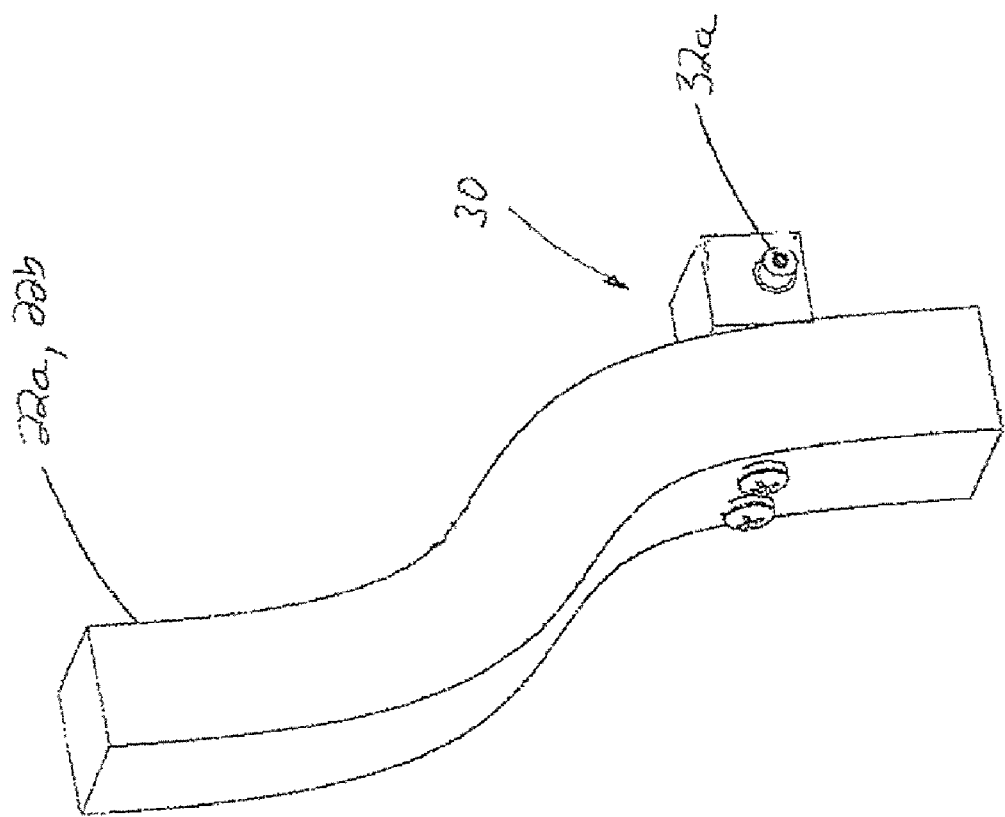
FIG. 4 is a perspective view of the manner in which a position sensor component is positioned on a part of the exercise device.

To provide the electrical stimulation necessary to perform the stepping exercise with the automated stimulation controller 100, it is necessary to evaluate the relative position and movement of the legs to know when to apply the stimulation. To achieve this, the preferred embodiment employs a position sensor 30, which may take the form of a magnetic proximity switch 32a mounted to each support 22a, 22b (see FIG. 4). A corresponding magnet 32b is mounted in a stationary fashion near the end of the range of motion, such as on or adjacent the stop 20 (see FIG. 2a-2c). As a result, the position of the foot plates 16a, 16b for at least one point in range of motion is known (that is, when the magnetic switch 32a is closed as the result of being in the proximity of the magnet 32b at the end of the range of motion of each leg when the corresponding support 22a, 22b engages the stop 20). However, different types of sensors or inputs could be used to determine the initial position, including for example an "initiation" button that can be pressed by the exercise subject to indicate the location of at least one of the foot plates 16a, 16b at a known position.

Figures 5A, 5B:
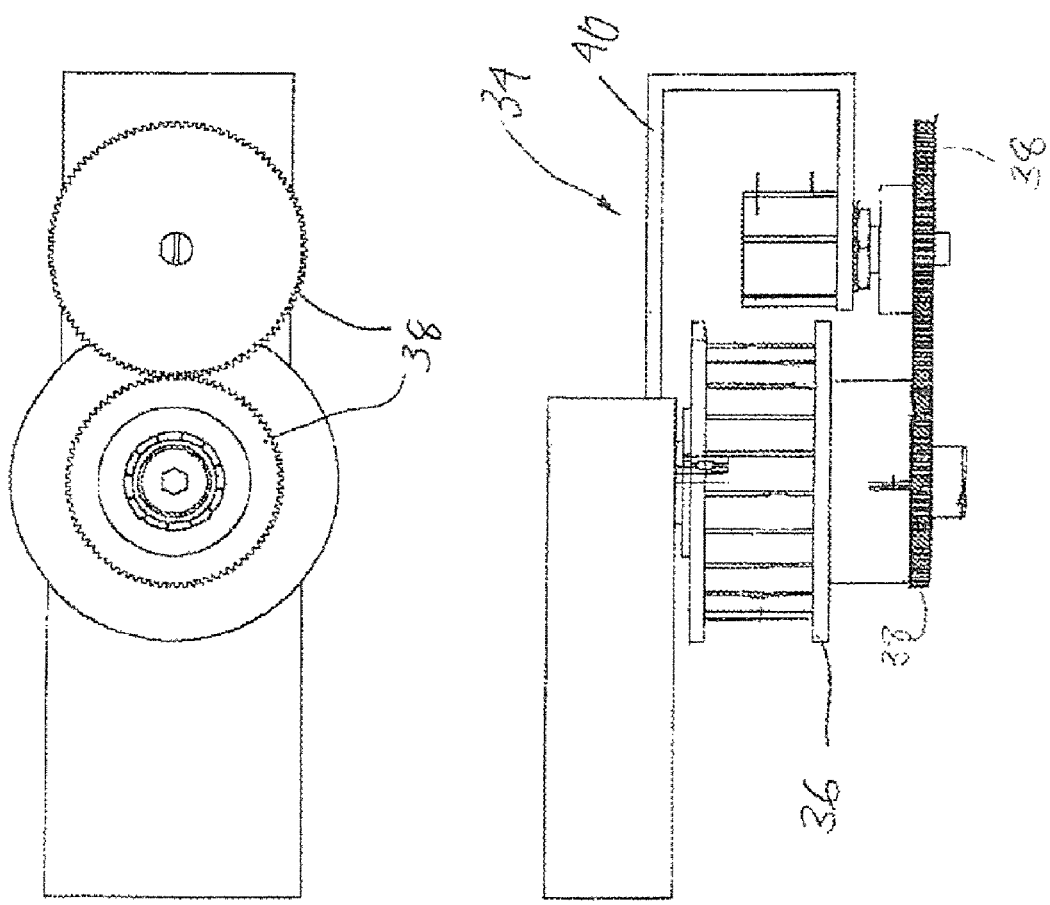
FIGS. 5a and 5b are top and side views of a motion sensor for associating with the exercise device.

As described in more detail below, generally knowing the point in the cycle of the legs is desirable to regulate the stimulation applied. To achieve this using the device 10 described above and shown in FIGS. 1a and 1b, a motion sensor 34, such as a potentiometer, is associated with a rotary part 36 of the device 10 that moves in a cyclical fashion in response to the relative movement of the plates 16a, 16b during the reciprocating movement of the legs. As shown in FIGS. 5a and 5b, this sensor 34 may form part of a sensor assembly, which includes gears 38 for transmitting the movement from the rotary part 36 to the potentiometer. A corresponding bracket 40 for associating with the base 12 or a corresponding stable support structure provides the desired mounting of the various components. Of course, motion sensing could be accomplished in many using, including by directly measuring joint angle of using the CK-5 sensor by customKYnetics, Inc. (as described in one or more of the above-referenced patent applications).

In the illustrated iteration, and as shown in FIG. 8, the stimulation controller 100 associated with the stimulator 50 determines a position error based on a predetermined desired position of plate 16a, 16b and the actual plate position determined from corresponding analog signal from sensor 34. This signal is then continuously used by controller 100 to "train," adjust and drive the stimulator 50 to cause the desired stimulation of the extensor muscles in the upper leg of the subject at a revised level and with adaptive feedback control based on the PGPS algorithm (in other words, in an adaptive pattern). As should be appreciated from FIG. 8, the resulting input to the device 10 is the force from the legs for moving the foot plates 16a, 16b on the left and right side, which are out of phase. The output from sensor 34 is then used to develop appropriate stimulation patterns for each leg (e.g., Z_left and Z_right), which through the stimulator 50 and associated electrodes reach the legs, which in turn input the force again to repeat the cycle.

In most cases, the exercise begins with the stimulation controller 100 having no information about the condition of the subject S, resistance settings, or other parameters that may affect the stimulation. The goal of the stimulation controller 100 is to develop a reciprocal, bilateral stepping pattern at a rate of N steps per minute, where N is constant for a given exercise protocol. Bilateral stimulation will begin at a predetermined level (and preferably in the manner described below), and the controller 100 will train and continually adjust the stimulation pattern to ensure the exercise is performed in the desired manner.

Preferably, and in order to maximize the benefit achieved from performing the exercise, the stimulation applied as the result of the controller 100 changes depending on whether certain conditions are met. For example, in applying control based on the PGPS algorithm, the exercise movement being controlled is presumed to be cyclic and repeatable. Specifically, the device 10 with which the PGPS algorithm is employed via controller 100 should return to a known state at the end of each cycle, such that training errors are associated with the stimulation delivered at the time that the errors occurred. Since this is not necessarily the case with a recumbent stepper device 10, it is desirable to monitor the stepping exercise on a cycle-to-cycle basis to determine whether stimulation (adaptive or otherwise) is necessary or appropriate.

Turning to FIG. 9, one manner of determining whether PGPS stimulation is appropriate is to evaluate if the extension half-cycle (that is, the extension phase of movement for the ipsilateral leg) begins with the contralateral leg at or near the end of the extension range of motion (e.g., the final 20% of the extension of range of motion, as determined by the output of the sensor 34). Unless the exercise begins in this "red zone," a non-adaptive (e.g., "fixed") stimulation mode is used instead of adaptive stimulation. In this mode, a fixed stimulation pattern is applied such that the legs are positioned appropriately for the start of the subsequent half-cycle and without using the PGPS algorithm. For example, the controller 100 may apply the stimulation in a fixed fashion at a specified rate until movement occurs, and then hold at the final point until either the corresponding footplate 16a or 16b enters the red zone or the cycle ends, at which point the stimulation may be turned off. As should be appreciated, the device 10 includes an inertial element, such as a flywheel. Thus, performing the stepping exercise using the device 10 involves not only initially accelerating this inertial element, but also maintaining its velocity. Since the joint torque requirements to accelerate this inertial element are far greater than those required to maintain its movement, it is also desirable to use the PGPS algorithm to apply the stimulation necessary only for maintaining the inertia, and initially accelerate the inertia by other means, such as by applying stimulation. The controller 100 uses the PGPS algorithm when the previous half-cycle started in the "red zone" of the contralateral leg and ended in the red zone of the ipsilateral leg (which means movement has occurred).

As noted above, the device 10 provides mechanical coupling of the foot plates 16a, 16b. Consequently, the muscles of the different legs work as antagonists if simultaneously activated. Accordingly, the preferred approach is to train the stimulation controller 100 for the contralateral leg as well as the ipsilateral leg for errors that occur during the ipsilateral extension half-cycle.

To further improve the exercise movement, stimulation may be simultaneously applied to the left and right legs in an antagonist relationship. An antagonist training coefficient may be used to control the distribution of error between the ipsilateral leg and contralateral leg (e.g., left and right) stimulation controllers forming part of controller 100. Left and right error, $\epsilon_{K\_L}$ and $\epsilon_{K\_R}$, are defined as:

$$\epsilon_{K\_L} = \epsilon_L \cdot (t<T/2) + k \cdot \epsilon_L \cdot (t>T/2)$$

$$\epsilon_{K\_R} = \epsilon_R \cdot (t>T/2) + k \cdot \epsilon_R \cdot (t<T/2)$$

where k is the antagonist training coefficient, t is time from the beginning of the current cycle, T is the cycle period, and (t<T/2), (t>T/2) are half-cycle binary terms with values 1 when t is within the ipsilateral leg half-cycle and 0 when in the contralateral leg half-cycle, $\epsilon_L$ and $\epsilon_R$ are position errors computed as the difference between the desired and measured position of the foot plates 16a, 16b. An antagonist training coefficient value of k=0.5 is believed to provide satisfactory performance, but could vary depending on the particular application.

Meaningful stimulation is undesirable when the corresponding leg is at or near full extension (as defined by the stop 20). Accordingly, it is preferred to monitor real-time and override stimulation specifications by either the stimulator 50 or controller 100 to reduce substantially and, most preferably, set stimulation to zero if the ipsilateral leg is in its "red zone." Stimulation to the contralateral leg is also discontinued to prevent unopposed co-stimulation from moving the ipsilateral leg from the "red zone." Most preferably, the cutoff is done in advance of reaching the maximum forward movement, as determined by stop, which may be assessed using the motion sensor 34 to determine the location of the leg in the range of motion.

The controller 100 in applying the PGPS algorithm also assumes that understimulation will result in an undershoot error (causing simulation to increase) and overstimulation will result in an overshoot error (causing stimulation to decrease). However, the stepping exercise performed using device 10 automatically limits the range of motion such that an overshoot error in the terminal exercise posture is not possible. This can prevent the controller from decreasing errant stimulation learned in the initial training cycles and can result in discontinuities in the stimulation profile.

Hence, the preferred application is to instantaneously switch the controller training mode when the foot plate 16a or 16b associated with the ipsilateral leg enters the "red zone" such that error is defined based on stimulation output rather than footplate position. As noted above, stimulation intensity is forced to zero when in the "red zone." Thus, the controller 100 when applying the PGPS algorithm automatically decreases stimulation when its output is being overridden.

The relationship between electrical stimulation intensity and muscle force (i.e., recruitment curve) is widely known to be nonlinear. The relationship typically follows a sigmoid shaped curve with a large initial deadband (i.e., stimulation results in zero muscle force). Rapid initial training is desired such that stimulation is increased above the level of the deadband within a very small number of cycles. However, if the controller 100 is adapted to train at this high rate then overtraining and potentially instability will result when stimulation reaches functional levels.

Accordingly, it is also desirable to define two sets of control modes: initial and maintenance. The controller 100 may switch to the maintenance mode set to train at a lower rate when the stimulation reaches functional levels. As a result, a more steady stimulation pattern may be provided.

With reference to FIGS. 10-11, a specific implementation of the above-described control is shown. The output (e.g. Z_left for the left side), may be the PGPS output, but in the illustrated embodiment two exceptions to this exist. Turning first to FIG. 10, a "comfort/creep" feature 60 of the control overrides PGPS output if the user indicates that the stimulation is excessive (such as if a corresponding input (e.g., button) associated with the stimulator 50 is pressed to voluntarily decrease the stimulation). This "comfort control" further includes a creep feature, which gradually increases stimulation back to the adaptive (PGPS) output with each passing cycle.

A second exception is an "override" feature 70 that sets the PGPS output to 0% if the corresponding footplate 16a, 16b is in the "red zone" (corresponding to the leg being fully extended). This prevents stimulation of the corresponding leg after it has reached the fully extended position. In order to provide reliable stimulation in the desired fashion, as noted above, this "red zone" check is performed in real time, rather than just at the start of the cycle (and most preferably using motion sensor 34).

Turning to FIG. 11, a training algorithm employed by controller 100 involves the application of the PGPS algorithm to develop a suitable stimulation output based on the determined error between the desired and actual position with one exception. The error evaluated during training is switched based on the "red zone." More specifically, if the corresponding plate 16a, 16b is not in this "red zone," then the position error (desired−actual) is used to train the controller 100. If in the "red zone" (stimulation=0%), then training error is instead based on the stimulation output itself. The result is that the controller 100 overrides the stimulation external to the PGPS and, therefore, the difference between the desired intensity (0%) and the actual (Z_PGPS) is the training error. This enables the controller 100 to decrease the stimulation being applied if the output is too high. A second feature 80 implements the antagonist training coefficient by scaling error by the factor K if the controller 100 during training determines that it is not in its extension half-cycle (which, again, means the extension phase of movement for the ipsilateral leg).

FIG. 12 provides a table showing various parameters that may be used in implementing the PGPS algorithm as part of the presently disclosed control. Of course, these parameters may vary depending on the particular application.

Starting, stopping, and monitoring of the exercise program may be accomplished though an input device associated with the stimulator 50, such as the CK200. Likewise, the subject may have a separate or satellite display 200 for showing the specifics of the regimen, such as when to start and stop, as well as the rest period or delay between exercise periods. Subject and assistant-accessible emergency stop buttons may also be provided to shut down the device 10 immediately in the event a problem arises during the regimen.

In addition to applying electrical stimulation directly to the muscles through electrodes placed on the skin of the subject, sensory (e.g., visual) stimulation may be provided as a means of encouraging or facilitating performance of the stepping exercise, such as by using the display 200 associated with the device 10 or a like adjacent medium having a graphical user interface (GUI) mounted within the view of the exercise subject.

This display 200 may display information to the subject regarding the parameters of the exercise, such as the amount of extension of each leg. The subject may then adjust the exercise in an effort to fully extend the legs, thus ensuring an even or symmetrical result (which can be especially important in situations where one of the legs is significantly stronger or more able than the other). The extension levels or amounts may be displayed numerically, graphically (such as bars), or simply by a series of indicators (such as LEDs, buzzers, recorded words of encouragement, other visual or audible cues) that activate.

In situations where the subject is not able to fully extend one or both of their legs, such as in the early days of rehabilitation after a stroke, the display 200 might instead show information regarding the position of the foot plates 16a, 16b as the legs move from the bent position, possibly along with a target position to be reached (which may be pre-set). This type of reinforcement or encouragement may be important in encouraging the subject to exercise and rewarding the performance, thus providing a sense of accomplishment.

In an alternate approach, the device 10 may also be used in connection with muscle-specific stimulation patterns set at a client-specified intensity level (e.g., a peak output value). For instance, with reference to FIG. 13, fixed stimulation patterns may be applied to the tibilais anterior, hamstrings, and general extensor (e.g., quadriceps or soleus/gastrocnemius) muscles throughout the range of movement (which is indicated as a percentage of the range of motion). This paradigm is designed primarily for use in a mode in which the primary movement of the legs during the exercise comes from a source other than the stimulation (e.g., voluntarily contributions by the subject (such as, for example, through the involved leg, the uninvolved leg, the upper extremities, such as by using handlebars 18a, 18b) or an external drive/prime mover), with the stimulation thus merely assisting the movement and providing a level of motor reeducation. Preferably, the stimulation would be initiated only after detecting at least one full cycle of movement, and would be terminated immediately if the movement stops or is too rapid or slow for the stimulation patterns to be applicable.

The foregoing descriptions of various embodiments of the invention are provided for purposes of illustration and not intended to be exhaustive or limiting. Modifications or variations are also possible in light of the above teachings. Also, it may be desirable for the adjustment in the level of electrical stimulation to be manually performed by the exercise subject or an assistant based on the performance parameters. During the adaptive feed-forward control, the revised level of stimulation may also be identical or substantially identical to the previous level of stimulation based on the detected level of the corresponding exercise parameter. The control disclosed as one aspect of the invention may have utility in exercises other than recumbent stepping, such as those involving reciprocal extension of the legs. The embodiments described above were chosen to provide the best application to thereby enable one of ordinary skill in the art to utilize the disclosed inventions in various embodiments and with various modifications as are suited to the particular use contemplated. All such modifications and variations are within the scope of the invention.

The invention claimed is:

1. A device for use by a human subject in performing a recumbent exercise using their hands, arms, legs, hips, knees and feet with the assistance of stimulation, comprising:
   a base;
   a seat supported by the base for receiving the subject;
   a pair of lower receivers adapted for independently engaging the subject's feet, the lower receivers constrained for moving alternatively and relative to the base along a first path of travel between a first, extended position with the corresponding leg at least partially bent and the corresponding knee positioned farther from the subject's upper torso and a second, retracted position with the corresponding leg more bent than in the first position and positioned closer to the upper torso;
   a pair of upper receivers adapted for independently engaging the subject's hands, the upper receivers pivotally connected to the base and constrained for alternately moving toward and away from the subject's body; and
   a stimulator adapted for electrically stimulating at least one muscle of at least one of the subject's legs as the first receivers move along the first path of travel in an alternating pattern.

2. The device of claim 1, wherein the stimulator is adapted to supply electrical pulses by way of electrodes applied to a skin surface adjacent the at least one muscle.

3. The device of claim 1, further including a controller for controlling the stimulator.

4. The device of claim 3, wherein the controller controls the stimulator to apply an adaptive or fixed pattern of stimulation depending on the position of the corresponding leg within an available range of motion.

5. The device of claim 3, wherein the controller is adapted to:
   control the stimulator during an initial phase in accordance with an initial mode; and
   determine whether the stimulation during the initial phase results in the alternating extension of both legs for at least two cycles, and then cause the stimulator to apply stimulation controlled in accordance with a maintenance mode.

6. The device of claim 3, further including a motion sensor for sensing movement of at least one of the legs along the path of travel and generating a corresponding output signal for use by the controller in controlling the stimulator to apply the adaptive or fixed pattern of stimulation.

7. The device of claim 3, wherein the controller causes the stimulator to at least reduce the applied stimulation to the at least one muscle of the leg before the corresponding lower receiver reaches the first extended position.

8. A method for assisting a human subject in performing a recumbent exercise using their hands, arms, legs, hips, knees and feet with the assistance of stimulation, comprising:
  positioning the subject on a seat;
  placing the subject's feet on corresponding lower receivers constrained to move reciprocally along a first path of travel between a first, extended position with the corresponding leg at least partially bent and the corresponding knee positioned away from the subject's upper torso and a second, retracted position with the corresponding leg more bent than in the first position and positioned closer to the subject's upper torso, such that the hip joint corresponding to each leg is being exercised during the movement;
  placing the subject's hands in contact with upper receivers pivotally mounted on a base and constrained for alternately moving toward and away from the subject's body; and
  electrically stimulating at least one of the leg muscles of the subject while the receivers move alternately along the path of travel.

9. The method of claim 8, further including the step of applying an adaptive or fixed pattern of stimulation depending on the position of the corresponding leg within a predetermined portion of an available range of motion.

10. The method of claim 8, further including the step of reducing the stimulation from a previously applied level if the leg is within a predetermined portion of an available range of motion.

11. The method of claim 10, wherein the step of reducing the stimulation comprises de-activating the stimulation.

12. The method of claim 10, wherein the step of stimulating comprises stimulating muscles of both legs simultaneously.

13. The method of claim 8, wherein the stimulating step is initially controlled in accordance with an initial mode, and further including the step of determining whether the stimulation results in the extension of both legs for at least two cycles, and then applying stimulation controlled in accordance with a maintenance mode.

14. A method of performing a recumbent exercise on a human subject, comprising:
  electrically stimulating at least one leg muscle at a predetermined level as the legs move alternately along a path of travel between a retracted position and an extended position during the exercise;
  measuring a position of the leg;
  comparing the measured position with a predetermined position to determine a variation;
  adjusting the predetermined level of electrical stimulation to a revised level based on the variation; and
  electrically stimulating at least a portion of the leg muscles at the revised level;
  wherein the subject's hands each associate with a moveable upper receiver, said upper receivers being pivotally mounted to a base and constrained to move in a reciprocating fashion, toward and away from the subject's body.

15. The method of claim 14, further including the step of positioning the subject on a seat.

16. The method of claim 14, further including the step of applying an adaptive or fixed pattern of stimulation depending on the position of the corresponding leg within an available range of motion.

17. The method of claim 14, further including the step of reducing the stimulation if the corresponding leg is within a predetermined portion of an available range of motion.

18. The method of claim 17, wherein the step of reducing the stimulation comprises stopping the stimulating step.

* * * * *